United States Patent
Mariani

(10) Patent No.: US 11,033,419 B2
(45) Date of Patent: Jun. 15, 2021

(54) MEDICAL DEVICE FOR PERFORMING ILEOSTOMIES AND/OR JEJUNOSTOMIES

(71) Applicants: EVOLUZIONE S.R.L., Rome (IT); SIDAM S.R.L., Frazione San Giacomo Ron (IT); Enrico Mariani, Trevi (IT); Emanuele Pagliacci, Gualdo Tadino (IT)

(72) Inventor: Enrico Mariani, Trevi (IT)

(73) Assignees: Evoluzione S.r.L., Rome (IT); Sidam S.r.l, Marandola (IT); Enrico Mariani, Trevi (IT); Emanuele Pagliacci, Gualdo Tadino (IT)

( * ) Notice: Subject to any disclaimer, the term of this patent is extended or adjusted under 35 U.S.C. 154(b) by 672 days.

(21) Appl. No.: 15/536,629

(22) PCT Filed: Dec. 18, 2015

(86) PCT No.: PCT/IB2015/059766
§ 371 (c)(1),
(2) Date: Jun. 16, 2017

(87) PCT Pub. No.: WO2016/098064
PCT Pub. Date: Jun. 23, 2016

(65) Prior Publication Data
US 2017/0367870 A1      Dec. 28, 2017

(30) Foreign Application Priority Data
Dec. 18, 2014   (WO) .................. PCT/IB2014/067094

(51) Int. Cl.
*A61F 5/445*       (2006.01)
*A61F 5/44*        (2006.01)

(52) U.S. Cl.
CPC ................ *A61F 5/445* (2013.01); *A61F 5/44* (2013.01); *A61F 2005/4455* (2013.01)

(58) Field of Classification Search
CPC combination set(s) only.
See application file for complete search history.

(56) References Cited

U.S. PATENT DOCUMENTS 4,311,148 A * 1/1982 Courtney .............. A61M 25/02
    604/175
4,368,739 A * 1/1983 Nelson, Jr. ......... A61M 25/1011
    604/101.05

(Continued)

FOREIGN PATENT DOCUMENTS

| WO | 2013/088234 A1 | 6/2013 | |
|---|---|---|---|
| WO | WO-2013088234 A1 * | 6/2013 | ........ A61M 25/1011 |
| WO | WO2013088234 A1 * | 6/2013 | ............ A61M 25/10 |

OTHER PUBLICATIONS

International Search Report and Written Opinion dated Apr. 19, 2016 from International Patent Application No. PCT/IB2015/059766 filed Dec. 13, 2015.

(Continued)

*Primary Examiner* — Guy K Townsend
(74) *Attorney, Agent, or Firm* — David B. Tingey; Bryant J. Keller; Kirton McConkie

(57) ABSTRACT

A medical device for performing ileostomies and/or jejunostomies, includes a tubular element defining a transit channel having a plurality of entry openings for the faeces, insertable inside the intestine of a patient, and an exit opening for the faeces, positionable outside the intestine. The tubular element includes a first section having the entry openings and a second section having the exit opening. First obstruction means is associated with the tubular element, insertable inside the intestine, and movable between tight and widened configurations. The entry openings are positioned upstream of the first obstruction means, the latter being placed between the first and the second sections. External retention means cooperate with the patient's body to block the posi- (Continued)

tion of the first obstruction means with respect to the body itself. Stiffening means are integrally associated with one another at respective extremities and prevent the first section from bending.

16 Claims, 5 Drawing Sheets

(56) References Cited

U.S. PATENT DOCUMENTS

| | | | | |
|---|---|---|---|---|
| 4,685,901 A * | 8/1987 | Parks | A61J 15/0015 604/103.03 |
| 5,071,405 A * | 12/1991 | Piontek | A61J 15/0015 604/103.03 |
| 5,098,378 A * | 3/1992 | Piontek | A61J 15/0015 604/500 |
| 5,112,310 A * | 5/1992 | Grobe | A61M 25/01 604/103.03 |
| 5,279,553 A * | 1/1994 | Winkler | A61B 17/3415 604/160 |
| 5,308,325 A * | 5/1994 | Quinn | A61J 15/0015 604/174 |
| 5,800,394 A * | 9/1998 | Yoon | A61B 17/00234 600/207 |
| 5,989,231 A * | 11/1999 | Snow | A61B 1/2736 600/109 |
| 6,010,453 A * | 1/2000 | Fiddian-Green | A61B 5/145 600/309 |
| 6,036,673 A * | 3/2000 | Quinn | A61M 25/0068 604/174 |
| 6,039,714 A * | 3/2000 | Cracauer | A61J 15/0034 604/103.03 |
| 6,315,789 B1 * | 11/2001 | Gragg | A61B 17/0401 604/175 |
| 6,322,495 B1 * | 11/2001 | Snow | A61B 1/00082 600/114 |
| 6,629,953 B1 * | 10/2003 | Boyd | A61M 25/0082 604/104 |
| 6,635,068 B1 * | 10/2003 | Dubrul | A61B 17/12022 606/200 |
| 6,765,122 B1 * | 7/2004 | Stout | A61F 13/00 602/41 |
| 7,331,980 B2 * | 2/2008 | Dubrul | A61B 17/12022 606/213 |
| 8,057,429 B2 * | 11/2011 | Nath | A61J 15/0049 604/97.02 |
| 8,147,449 B2 * | 4/2012 | Gobel | A61M 39/0247 604/96.01 |
| 9,198,835 B2 * | 12/2015 | Swisher | A61B 1/00144 |
| 9,211,234 B2 * | 12/2015 | Tai | A61J 15/0038 |
| 9,232,917 B2 * | 1/2016 | Addington | A61B 5/227 |
| 9,283,151 B2 * | 3/2016 | Porreca, Jr. | A61J 15/0069 |
| 9,492,644 B2 * | 11/2016 | Tai | A61M 25/09 |
| 10,117,738 B2 * | 11/2018 | Demehri | A61M 29/02 |
| 10,130,559 B2 * | 11/2018 | Tai | A61M 25/09 |
| 2003/0199913 A1 * | 10/2003 | Dubrul | A61B 17/12113 606/191 |
| 2003/0225369 A1 * | 12/2003 | McMichael | A61M 39/0247 604/104 |
| 2003/0225392 A1 * | 12/2003 | McMichael | A61J 15/0069 604/509 |
| 2003/0225393 A1 * | 12/2003 | McMichael | A61J 15/0023 604/513 |
| 2006/0079845 A1 * | 4/2006 | Howard | A61M 25/04 604/175 |
| 2007/0049904 A1 * | 3/2007 | Deutsch | A61M 25/0045 604/540 |
| 2009/0005802 A1 * | 1/2009 | Williams | A61J 15/0038 606/191 |
| 2009/0216186 A1 * | 8/2009 | Nath | A61J 15/0015 604/97.02 |
| 2009/0312701 A1 * | 12/2009 | Gobel | A61J 15/0057 604/96.01 |
| 2009/0318757 A1 * | 12/2009 | Singh | A61J 15/0026 600/109 |
| 2009/0318798 A1 * | 12/2009 | Singh | A61B 1/012 600/424 |
| 2009/0326513 A1 * | 12/2009 | Deutsch | A61B 17/221 604/540 |
| 2011/0098660 A1 * | 4/2011 | Porreca, Jr. | A61J 15/0069 604/246 |
| 2012/0203175 A1 * | 8/2012 | Sun | A61B 17/3403 604/103.09 |
| 2012/0245510 A1 * | 9/2012 | Rakower | A61M 13/003 604/26 |
| 2013/0237755 A1 * | 9/2013 | Singh | A61B 1/012 600/109 |
| 2014/0073853 A1 * | 3/2014 | Swisher | A61B 1/051 600/104 |
| 2014/0121646 A1 * | 5/2014 | Lodin | A61K 33/00 604/514 |
| 2014/0180242 A1 * | 6/2014 | Tai | A61M 25/065 604/506 |
| 2015/0257695 A1 * | 9/2015 | Addington | A61B 5/205 600/301 |
| 2016/0213461 A1 * | 7/2016 | Demehri | A61F 2/04 |
| 2017/0035660 A1 * | 2/2017 | Tai | A61M 29/02 |
| 2017/0367870 A1 * | 12/2017 | Mariani | A61F 5/445 |

OTHER PUBLICATIONS

International Search Report and Written Opinion dated Aug. 21, 2015 from International Patent Application No. PCT/IB2014/067094 filed Dec. 13, 2014.

* cited by examiner

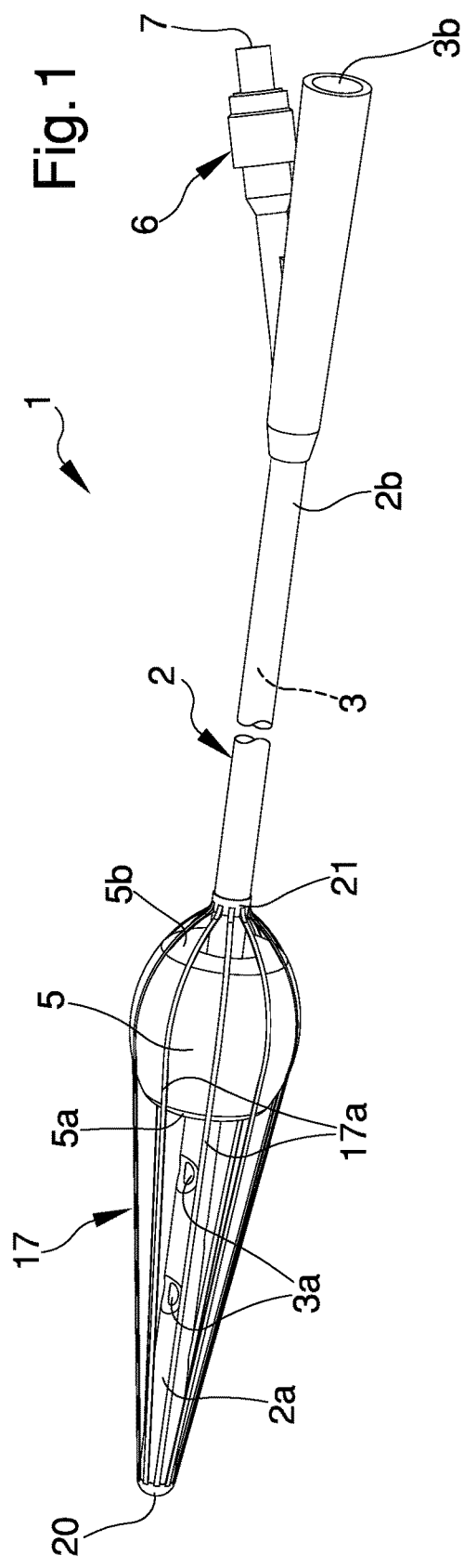

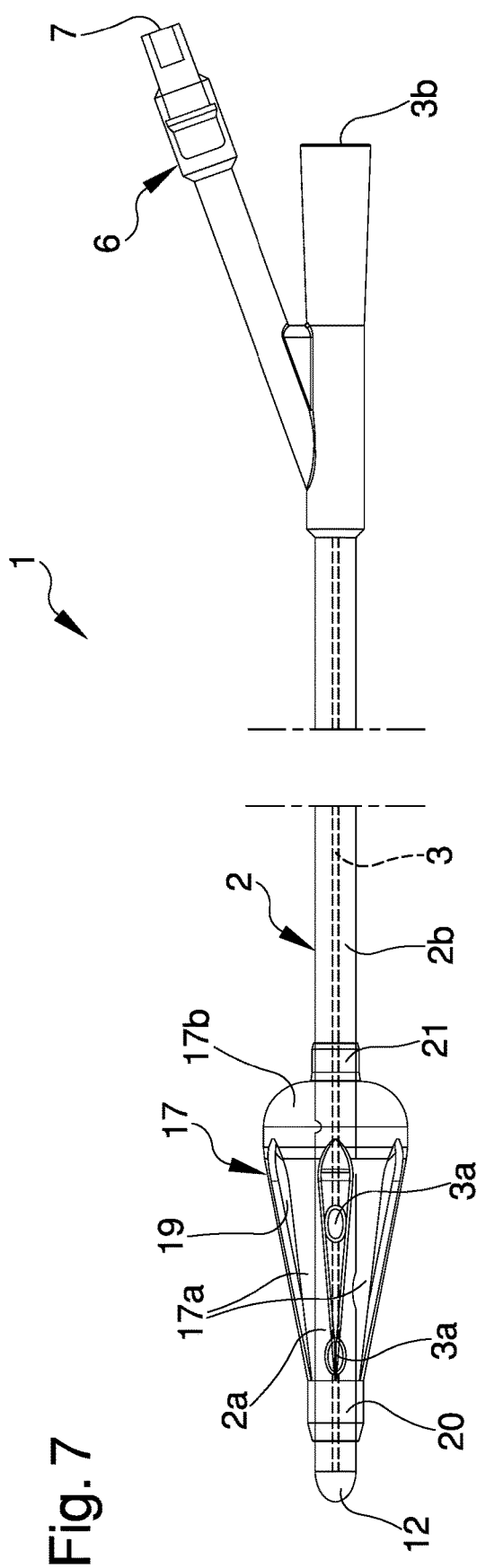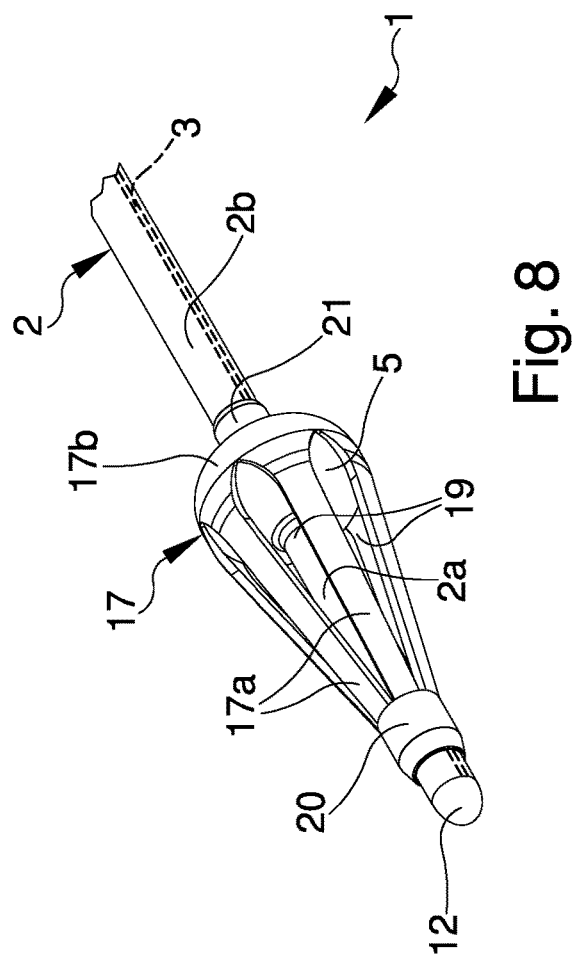

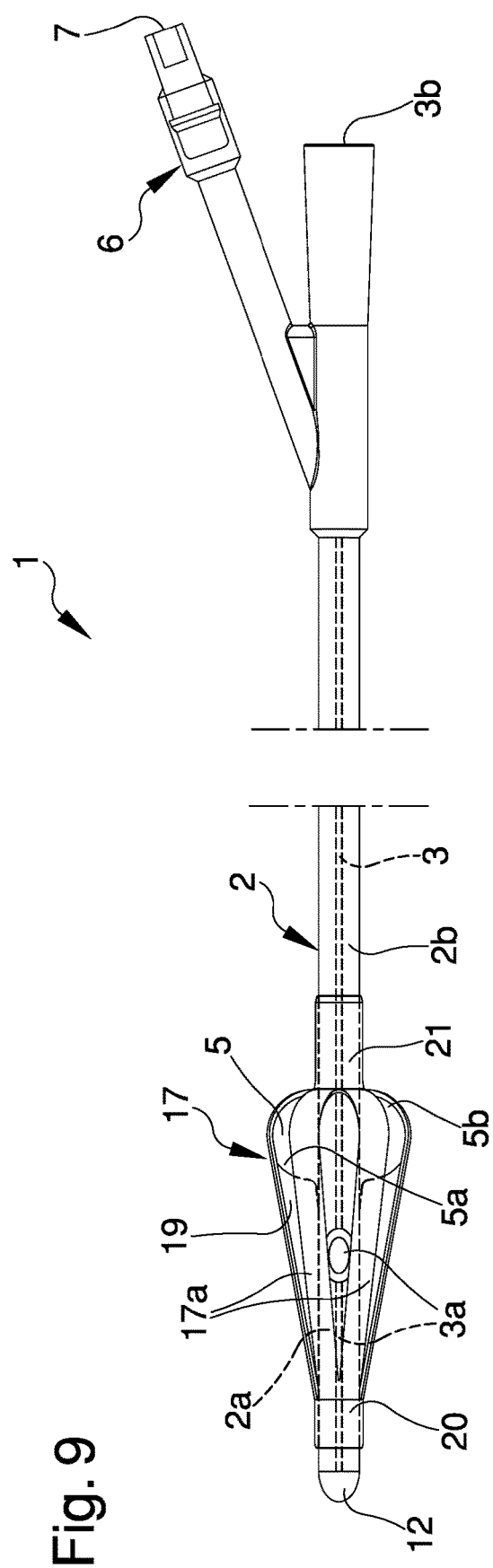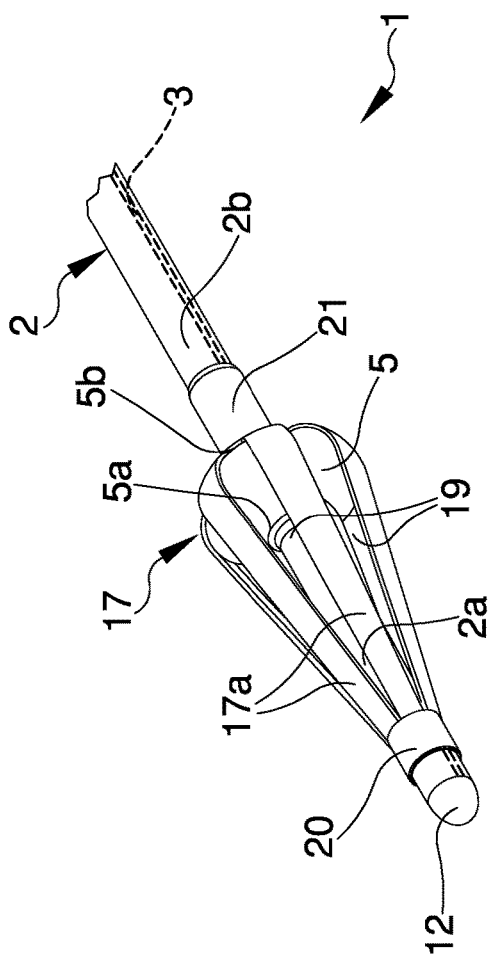

MEDICAL DEVICE FOR PERFORMING ILEOSTOMIES AND/OR JEJUNOSTOMIES

TECHNICAL FIELD

The present invention relates to a medical device for performing ileostomies and/or jejunostomies.

BACKGROUND ART

In medical practices it is known that in the case of diseases of the intestine, such as Chron's disease, ulcerative colitis, perforated diverticulitis, cancer, etc. . . . , or when natural evacuation of faeces is no longer possible, it becomes necessary to deviate the dejections of the digestive tract outwards.

For example, in the case of intestinal cancer following which a surgical resection of the intestine itself has been performed with consequent anastomosis, the flow of faeces must be deviated to prevent these reaching the operated area and infecting it.

For this purpose, standard procedure is to perform an ileostomy, i.e., to connect the intestine to an external container through a stoma, i.e., a hole made in the abdominal wall.

More in particular, the ileostomies can be of a temporary or permanent type depending on the disease.

As it is easy to appreciate, temporary ileostomies are used for the purpose of temporarily suspending, for a period of around three months, the functions of a section of the intestine, after which the normal functionality of the latter is restored, while permanent ileostomies are used in the case of chronic diseases and therefore envisage a permanent deviation of the intestine.

The present description relates mainly to the case of temporary ileostomies.

More in detail, currently, temporary ileostomies are performed by passing a loop of the ileum, positioned upstream of the area to be safeguarded with respect to the direction of forward movement of the dejections, through an opening made in the abdominal wall (stoma). To prevent the ileum retracting into the abdominal cavity a bar is generally fitted in the loop.

At this point, the intestine is cut off at the loop thus extracted thereby separating the ileum into two sections, one connected to the stomach and from which the faeces are evacuated, the other instead communicating with the area to be safeguarded and the functions of which are therefore suspended.

Once the healing process of this intestinal section is completed, the two sections of the ileum are again surgically closed.

This procedure to perform a temporary ileostomy has a number of drawbacks.

In fact, both performing the ileostomy and removing it require respective surgical operations performed with general anaesthetic.

This naturally involves not only a lot of discomfort, both physical and psychological, for the patient, but also long periods of postoperative recovery. Furthermore, such procedure also involves high costs for the health facilities because of the surgical operations that have to be performed to treat the diseases involving the intestine and which, as is known, require the use of specific equipment and qualified medical staff. Such costs inevitably tend to have repercussions on the national health system.

Furthermore, the medical staff and the equipment used for such operations are obviously subtracted from the performance of other surgical operations, hence an obvious extension of waiting times ensues.

The procedure for performing the temporary ileostomies of the type described above thus shows itself to be costly, in view of its complexity, both economically and in terms of health logistics.

DESCRIPTION OF THE INVENTION

The main aim of the present invention is to provide a medical device that allows providing an ileostomy and/or jejunostomy, in a considerably easier and more practical manner than the procedures of known type.

In particular, the present invention proposes to provide a device that allows reducing the number of operations required for the application and removal of an ileostomy and/or jejunostomy, considerably reducing the discomfort for the patient and the postoperative recovery period.

Within this aim, one object of the present invention is to also cut the health costs related to the treatment of the diseases requiring the application of an ileostomy and/or jejunostomy and to contribute to the relief of the national health system in managing the operations, so as to cut waiting times and thus optimize resources.

Another object of the present invention is to provide a medical device for ileostomies and/or jejunostomies which allows to overcome the mentioned drawbacks of the prior art within the ambit of a simple, rational, easy and effective to use as well as low cost solution.

The above mentioned objects are achieved by the present medical device for performing ileostomies and/or jejunostomies, according to claim 1.

BRIEF DESCRIPTION OF THE DRAWINGS

Other characteristics and advantages of the present invention will become better evident from the description of a preferred but not exclusive embodiment of a medical device for ileostomies and/or jejunostomies, illustrated by way of indicative, but not limitative example in the accompanying drawings in which:

FIG. 1 is an axonometric view of a medical device according to the invention in a first embodiment;

FIG. 2 is an enlargement of a detail of the device of FIG. 1;

FIG. 7 is a side elevation view of a medical device according to the invention in a second embodiment;

FIG. 8 is an axonometric view of a detail of the device of FIG. 7;

FIG. 9 is a longitudinal section of the medical device according to the invention in a third embodiment;

FIG. 10 is an axonometric view of a detail of the device of FIG. 9.

EMBODIMENTS OF THE INVENTION

Figure 3:
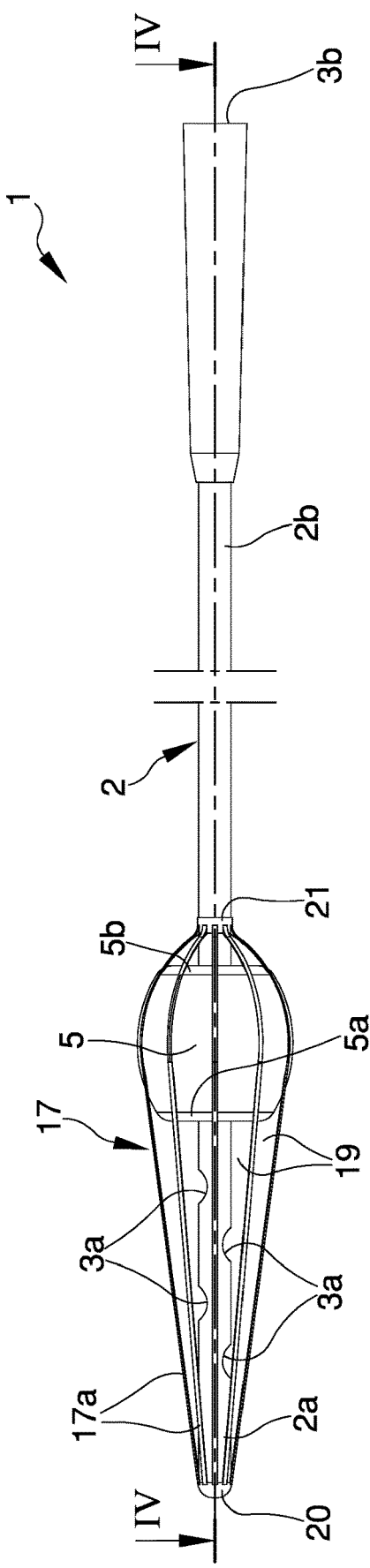
FIG. 3 is a side elevation view of the device of FIG. 1.

With particular reference to such figures, the reference number 1 globally designates a medical device for performing ileostomies and/or jejunostomies, particularly of temporary type.

The device 1 comprises at least a tubular element 2 wherein is defined at least a transit channel 3 having a plurality of entry openings 3a for the faeces, insertable inside the intestine I of a patient, and at least an exit opening 3b for the faeces, positionable outside the intestine I.

The tubular element 2 is made of a matt radium material, e.g., silicone or polyurethane More in particular, the tubular element 2 comprises at least a first section 2a in which are obtained the entry openings 3a and at least a second section 2b in which is obtained the exit opening 3b.

The first section 2a is insertable inside the intestine I of the patient through a stoma, e.g. made in the abdomen A of same to perform an operation in laparoscopy, such as a surgical operation involving the resection of a section of the ileum.

Advantageously, the entry openings 3a are defined at the lateral surface of the first section 2a.

Preferably, at least a part of the entry openings 3a is arranged along the longitudinal extension of the first section 2a.

The entry openings 3a are distributed in such a way as to allow draining along the substantial totality of the lateral surface of the first section 2a.

More in particular, the entry openings 3a are longitudinally staggered the one to the other and are arranged along a theoretical spiral wrapped around the first section 2a.

Suitably, the entry openings 3a have a substantially elliptical conformation. More in detail, the major axis of the entry openings 3a is arranged substantially parallel to the longitudinal extension of the first section 2a.

The entry openings 3a are of such size as to allow the back flow of the faeces inside the duct 3 and at the same time prevent the weakening of the tubular element 2. The elliptical conformation of the entry openings 3a does in fact allow having the greatest back flow possible, the weakening of the first section 2a being equal.

In this respect, i.e., to permit the presence of an adequate number of entry openings 3a having the aforementioned dimensions, the length of the first section 2a is substantially between 8 cm and 10 cm.

The axial extremity of the first section 2a, identified in the illustrations by the reference number 12, is suitably reinforced, e.g., by means of a spiralled tip or the like, to ensure easier insertion inside the first part I' of the intestine I.

The second section 2b instead is meant to be arranged outside the intestine I and the exit opening 3b, arranged at its axial extremity, and can be associated with a container for collecting the faeces not shown in the illustrations.

Preferably, the second section 2b has a length substantially equal to 40 cm.

The device 1 then comprises at least first obstruction means 5 of at least an area Z of the intestine I associated with the tubular element 2, insertable inside the intestine itself and configured so as to prevent the transit of the dejections through such area Z.

The first obstruction means 5 are able to isolate the part of the intestine I arranged downstream of the area Z with respect to the direction of forward movement of the faeces.

The first obstruction means 5 are therefore able to separate the intestine I into two parts, a first part I' and a second part I". The first and the second parts I' and I" are arranged upstream and downstream respectively of the first obstruction means 5 with respect to the direction of forward movement of the faeces. The first part I' is therefore in communication with the patient's stomach, while the second part I" corresponds to the part the functionalities of which are to be suspended inasmuch as it comprises the portion to be safeguarded, e.g., the portion in which an anastomosis has been performed.

The entry openings 3a, and therefore also the relative first section 2a, are intended to be housed in the first part I' of the intestine I, i.e., upstream of the first obstruction means 5 always with respect to the direction of forward movement of the faeces, in such a way as to intercept the dejections arriving from the digestive tract.

The first obstruction means 5 are configured so as to prevent the transit of the faeces coming from the first part I' to the second part I".

Suitably, the first obstruction means 5 are placed between the first section 2a and the second section 2b.

In detail, the first obstruction means 5 comprise a first portion 5a pointed towards the first section 2a and a second portion 5b pointed towards the second section 2b.

Advantageously, the first obstruction means 5 are movable between a tight configuration, to allow them to be inserted in the intestine I through the stoma, and a widened configuration, wherein they fully obstruct the area Z of the intestine I to prevent the transit of the faeces from the first part I' towards the second part I".

Preferably, the first obstruction means 5 consist of an inflatable balloon. Such inflatable balloon 5 is arranged outside the tubular element 2 and is substantially deflated in the tight configuration and inflated in the widened configuration.

More in particular, the device 1 comprises starting means 6 of the balloon 5. The starting means 6 comprise a gap 7 for the entry and exit of the air communicating with the balloon 5 through a duct not visible in detail in the illustrations and associated with the tubular element 2. The duct placing in communication the gap 7 with the balloon 5 is distinct from the transit channel 3.

The starting means 6 also comprise a check valve, not visible in detail in the illustrations, able to prevent the air contained in the balloon 5 from accidentally coming out and controllable by an operator to permit the air to flow outwards. According to the invention, the device 1 also comprises stiffening means 17 associated with the first section 2a to prevent this collapsing.

Advantageously, the stiffening means 17 comprise a plurality of elastically deformable stiffening elements 17a which externally cover the first section 2a and the first obstruction means 5.

More in detail, such stiffening elements 17a therefore move from an idle configuration, which corresponds to the tight configuration of the balloon 5 and wherein they substantially adhere to the tubular element 2, to an active configuration (shown in the illustrations), which corresponds to the widened configuration of the balloon 5 and wherein they are distanced from the profile of the tubular element 2 taking on a divergent conformation proceeding from the free extremity 12 towards the balloon itself.

The conformation of the stiffening elements 17a is therefore influenced by that of the first obstruction means 5.

In the active configuration, shown in the illustrations, the stiffening elements 17a are therefore tensioned by the balloon 5 so as to confer rigidity to the first section 2a in order to prevent the latter bending on itself and obstructing the entry openings 3a.

The stiffening elements 17a are for example made of a material such as polyurethane or silicone.

Preferably, as can be seen in the first embodiment shown in the figures from 1 to 6, the stiffening elements 17a have a substantially threadlike conformation.

In the second and third embodiments shown in FIGS. 7, 8, 9 and 10, on the other hand, the stiffening elements 17a are ribbon shaped.

In detail, the ribbon shaped allows to reduce the number of the stiffening elements 17a in front of equal upholstered surface of the first obstruction means 5.

More in particular, the stiffening elements 17a are separated from one another to define a plurality of through gaps 19, suitable for allowing the transit of the intestinal contents towards the entry openings 3a. As shown in the illustrations, the gaps 19 are diverging proceeding towards the first obstruction means 5.

In the preferred embodiment shown in the illustrations, the stiffening elements 17a extend between the free extremity 12 of the first section 2a and the first obstruction means 5, in such a way as to maintain a fixed distance between them.

More in detail, the stiffening elements 17a have one extremity associated in the proximity of the free extremity 12 and the opposite extremity associated with the tubular element 2 in the proximity of the first obstruction means 5 and on the opposite side with respect to the free extremity 12.

Advantageously, the stiffening elements 17a are integrally associated the one with the other to form a single body.

According to the invention, the stiffening elements 17a are integrally associated with one another at their respective extremities.

More in particular, the single body defined by the stiffening elements 17a has a first extremity, identified in the illustrations by the reference number 20, which is associated at the first section 2a, and a second extremity 21 associated at the second section 2b.

In the first embodiment shown in the figures from 1 to 6, the stiffening elements 17a have an extremity associated with the free extremity 12 and the opposite extremity associated with the second section 2b in the proximity of the first obstruction means 5. In this first embodiment, the first extremity 20 is closed to define an abutting surface against which rests the free extremity 12 and the second extremity 21 defines a through opening 22 through which the tubular element 2 is inserted.

In the second embodiment shown in the FIGS. 7 and 8, on the other hand, the stiffening elements 17a have a first extremity 20 associated with the first section 2a and a second extremity 21 associated with the second section 2b, both of which define a relative through opening through which the tubular element 2 is inserted.

In this second embodiment, furthermore, the stiffening elements 17a define, at the second extremity 21, a full portion 17b able, in the active configuration taken on by the stiffening elements themselves, to cover at least partially the first obstruction means 5. The full portion 17b therefore delimits, at the top, the gaps 19 and is positioned between these and the second extremity 21.

The presence of the full portion 17b enables the balloon 5 to inflate in a symmetrical and uniform way.

In the third embodiment shown in the FIGS. 9 and 10, the stiffening elements 17a have the first extremity 20 associated with the first section 2a and the second extremity 21 associated with the second section 2b, both of which define, similarly to the second embodiment, a relative through opening through which the tubular element 2 is inserted.

In the third embodiment, the second extremity 21 is placed in correspondence of the first obstruction means 5.

Advantageously, the second extremity 21 is placed in correspondence of the second portion 5b; this impedes the formation of an empty space between the second extremity 21 and the second portion itself, guaranteeing the inflation of the balloon 5 in a symmetrical and uniform way.

In an alternative embodiment, not shown in the illustrations, the device 1 also comprises second obstruction means of at least a second area of the intestine arranged along the tubular element and separated from the first obstruction means, the second obstruction means being insertable inside the intestine itself and being shaped so as to prevent the transit of the intestinal contents through the second area of the intestine.

The second obstruction means are placed between the entry openings 3a and the exit opening 3b.

More in particular, the second obstruction means are placed between the first obstruction means 5 and the exit opening 3b.

The second obstruction means are therefore arranged in series to the first obstruction means 5 along the tubular element 2 and are able to define a further barrier to the transit of the intestinal contents, so as to prevent any parts of the latter which have come out between the first obstruction means 5 and the intestinal wall from reaching the area to be safeguarded of the intestine itself.

The second obstruction means are therefore arranged downstream of the first obstruction means 5 in the direction of forward movement of the intestinal contents.

Between the first and the second obstruction means are also suitably placed further entry openings suitable for draining, inside a further transit channel, this too defined inside the tubular element 2, any parts of the intestinal contents which have come out through the first obstruction means 5. Such further transit channel can coincide with the transit channel 3 or can be distinct from this.

The retention means 8 comprise at least a perforated retention element 18 fitted sliding over the second section 2b. The retention element 18 defines a contact surface intended to rest against the patient's body.

Figure 4:
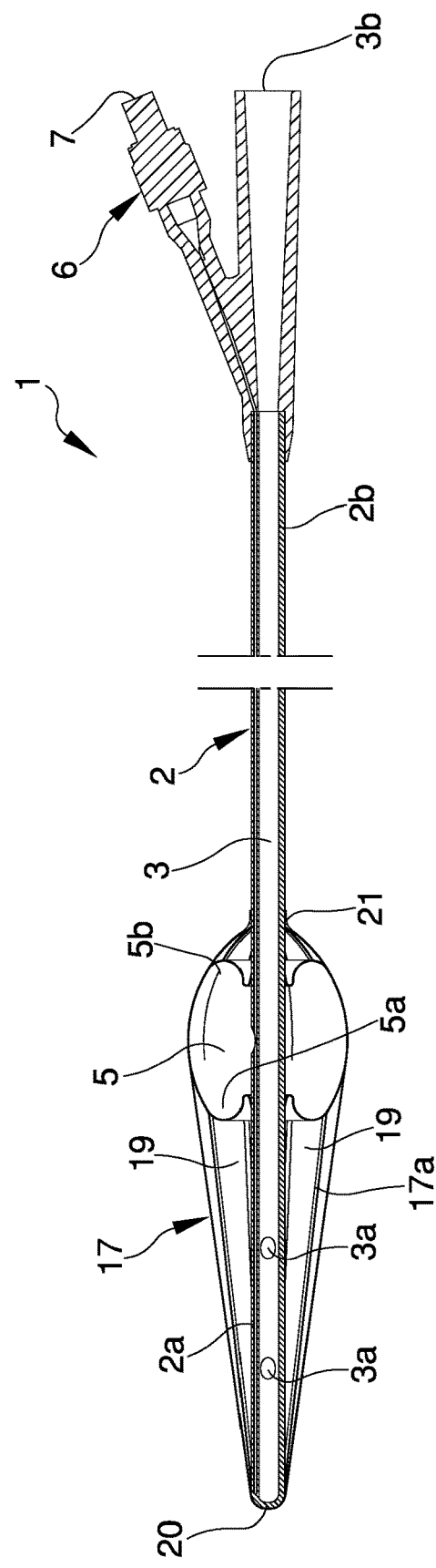
FIG. 4 is a longitudinal section of the device of FIG. 1.
Figure 5:
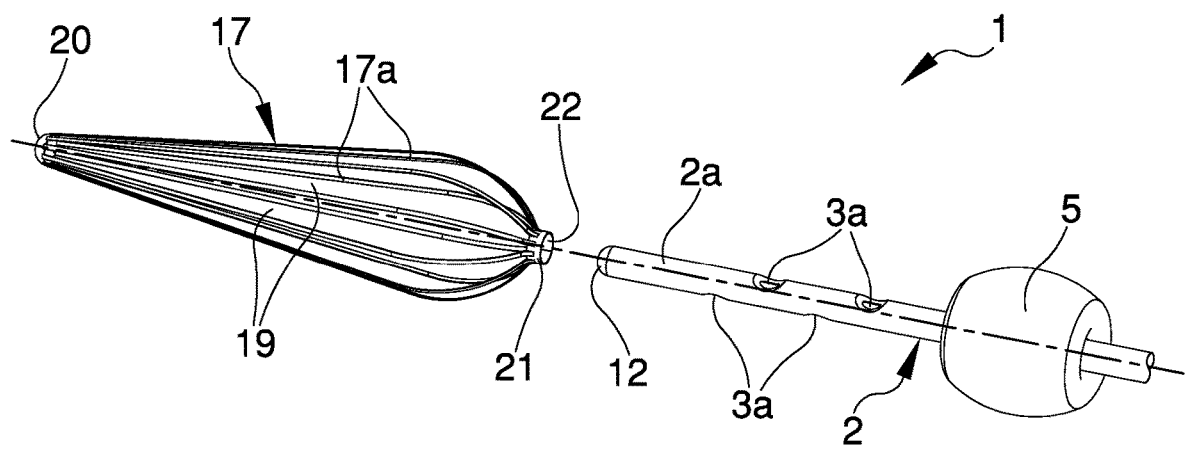
FIG. 5 is an enlargement of the stiffening means of the device of FIG. 1.
Figure 6:
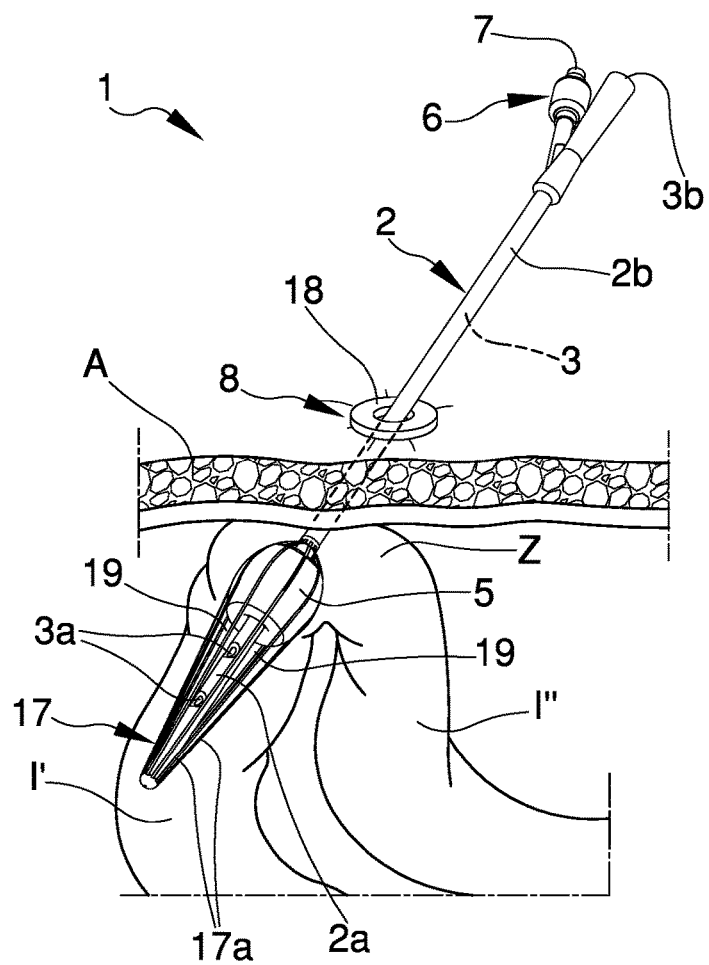
FIG. 6 is an axonometric view of the device of FIG. 1 inserted within the intestine of a patient.

In the embodiment in FIG. 4, the retention element 18 is of the type of a disc having a central through hole for the insertion through it of the second section 2b.

Preferably, the retention element 18 is made of a material with a high friction coefficient, e.g., of silicone, in such a way as to make its sliding difficult with respect to the tubular element 2.

In use, therefore, the retention element 18 is made to slide on the second section 2b until its contact surface is brought to rest against the patient's abdominal wall A.

Different embodiments of the retention element 18 cannot however be ruled out, not shown in the attached illustrations and having, e.g., guide means of the second section 2b. Such guide means are e.g. made up of a housing seat of a portion of the second section 2b, which extends along a substantially sloping direction with respect to the axis of the through hole, the latter not being visible in detail in the illustrations. More in particular, the housing seat extends along a direction substantially parallel with the contact surface of the retention element 18.

In a further embodiment, the retention element 18 can also comprise fastening means, e.g., made up of one or more through holes, associable with the patient's body, e.g., by means of suture.

The present invention operates as follows.

It is presumed that a stoma has already been performed on the patient's abdomen A, e.g., to carry out an operation in laparoscopy on his/her intestine, or specifically to make the ileostomy and/or jejunostomy.

At the end of the surgical operation involving the intestine, the tubular element 2 is made to pass through the above-mentioned stoma, in such a way as to insert its first section 2a inside the intestine I, at the area Z located upstream of the operated part with respect to the direction of forward movement of the faeces. The tubular element 2 is pushed inside the intestine I in such a way that the entry openings 3a are directed towards the patient's stomach.

The first obstruction means 5 are also introduced inside the intestine I.

Obviously, during the insertion of the tubular element 2 inside the intestine I, the balloon 5 is in tight configuration in order to make its transit through the stoma easier. The result therefore is that, during this phase, the stiffening elements 17a are also in idle configuration.

Once the tubular element 2 has therefore been inserted in the way just described and after the above surgical operation has terminated, the part of the intestine involved in the operation is isolated and the ileostomy and/or the jejunostomy is performed.

More in particular, the balloon 5 is brought to the widened configuration by blowing air through the gap 7. This way, the balloon 5 is inflated and widens to occupy the entire section of the area Z in which it is inserted, obstructing it.

The balloon 5 is deformable and when it is in widened configuration, it therefore conforms to the inner walls of the intestine I.

Following the inflation of the balloon 5, the stiffening elements 17a also move from their idle configuration towards the active configuration, wherein they are tensioned by effect of the widening of the balloon itself so as to give rigidity to the first section 2a. The stiffening elements 17a are therefore suitable, in their active configuration, for maintaining the first section 2a substantially extended. As has been said above, the first section 2a is arranged, during use, upstream of the first obstruction means 5, i.e., along the first part I' of the intestine I.

Suitably, by applying a traction force on the second section 2b which has remained outside the intestine I and which protrudes from the patient's body, the balloon 5 and therefore the area Z of the intestine itself is brought at the stoma.

At this point, the retention element 18 is brought at the patient's body making it slide along the second section 2b and bringing its contact surface to rest against the patient's skin.

This way, the tubular element 2 is blocked with respect to the patient's body inasmuch as the retention element 18 and the balloon 5 are arranged on opposite sides of the stoma.

The dejections coming from the patient's stomach and which cross the first part I' of the intestine I are therefore intercepted by the balloon 5 which prevents their forward movement in the second part I'' and they therefore enter the transit channel 3 through the entry openings 3a defined along the first section 2a and arranged in such a way as to substantially cover all its lateral wall.

The faeces therefore cross the transit channel 3 until they reach the exit opening 3b through which they are conveyed into the specific collection container.

To remove the ileostomy and/or the jejunostomy the balloon 5 simply has to be deflated by means of the valve located in the proximity of the gap 7 and the tubular element 2 extracted through the stoma.

Once the tubular element 2 has been removed, the intestine I is again without impediments and can therefore again start its normal operation, whereby the dejections from the stomach cross the area Z, which is now free, and move along the second part I'' of the intestine itself.

The stoma obtained in the patient's abdomen A is then suitably medicated and protected until complete healing and cicatrisation.

The present invention therefore relates to a medical device 1 comprising: a tubular element 2 wherein is defined a transit channel 3 having a plurality of entry openings 3a and at least an exit opening 3b, and comprising at least an inflatable balloon 5, used to perform the ileostomies in the treatment of intestinal diseases.

It has in fact been ascertained how the described invention achieves the proposed objects and in particular the fact is underlined that the medical device for performing ileostomies according to the invention permits considerably limiting invasive operations on the patient for the application and removal of an ileostomy.

In fact, the device according to the invention is fitted during the surgical operation aimed at treating the disease affecting the intestine and its removal occurs in day surgery without the use of any anaesthesia.

In particular, in the case of surgical operations performed in laparoscopy, the holes used for the operation can be exploited such as stoma for fitting the device according to the invention, thus reducing operations on the patient to the utmost.

This also means that recovery times are also considerably reduced with respect to the use of known techniques, inasmuch as the removal of the ileostomy occurs in just a few seconds and the patient, besides not having to undergo a further operation, with consequent loss of blood and correlated risks, does not even have to overcome a new general anaesthesia.

The presence of the stiffening means, furthermore, ensures that, in use, the section of the tubular element on which the entry openings are defined, does not bend on itself, thereby obstructing the openings themselves. In other words, the stiffening means ensure the full functionality of the device forming the subject of the present invention during its use.

The invention claimed is:

1. A medical device for performing ileostomies and/or jejunostomies, comprising:
    a tubular element comprising: a transit channel therethrough; a plurality of entry openings; and an exit opening; said tubular element being insertable within an intestine, wherein said tubular element further comprises a first section having said entry openings and configured for receiving faeces from said intestine; a second section having said exit opening configured for being positioned outside said intestine; and a middle portion between said first and second sections;
    a first obstruction having opposite proximal and distal portions and extending around said middle portion of said tubular element between said first and second sections, said first obstruction configured to be: insertable with said tubular element inside said intestine in a tight configuration, and expandable to a widened configuration to prevent transit of said faeces through said intestine where said first obstruction has been inserted;
    wherein said first section of said tubular element is attached to a distal ring- or cap-shaped first extremity attached to distal ends of a plurality of elastically deformable stiffening elements comprising proximal ends and said distal ends, and surrounding and externally covering at least a portion of said first section, said first obstruction covering at least a portion of said middle portion; and a stiffening member to help prevent at least said first section from bending and comprising said plurality of said elastically deformable stiffening elements; wherein said elastically deformable stiffening elements are integrally associated with one another at said distal ends attached to said distal ring- or cap-shaped first extremity at a distal end of said first section of said tubular element; and a proximal ring-shaped second extremity defining a through opening through which a proximal end of said middle portion of said tubular element is provided; and wherein said proximal ends of said plurality of elastically deformable elements are attached to said ring-shaped second extremity.

2. The device according to claim 1, wherein said elastically deformable stiffening elements have a substantially threadlike conformation and are separated from one another to define a plurality of through gaps.

3. The device according to claim 1, wherein said elastically deformable stiffening elements are substantially ribbon shaped.

4. The device according to claim 1, wherein said elastically deformable stiffening elements have an extremity associated with said first section in proximity of said free extremity and an opposite extremity associated with said second section in proximity of said first obstruction.

5. The device according to claim 1, wherein said elastically deformable stiffening elements are movable, by effect of a transition of said first obstruction from said tight configuration towards said widened configuration, between an idle configuration, wherein said elastically deformable stiffening elements substantially follow a profile of said first section, and an active configuration, wherein said elastically deformable stiffening elements are distanced from an external surface of said first section taking on a divergent conformation outwards proceeding from said free extremity towards said first obstruction.

6. The device according to claim 1, wherein said elastically deformable stiffening elements are associated with one another to define a first extremity arranged at said first section and a second extremity arranged at said second section, where said first and second extremities define a respective through opening through which said tubular element is insertable.

7. The device according to claim 6, wherein said second extremity is placed in correspondence of said first obstruction.

8. The device according to claim 6, wherein said first obstruction comprises a first portion pointed towards said first section and a second portion pointed towards said second section, said second extremity being placed in correspondence with said second portion.

9. The device according to claim 6, wherein said elastically deformable stiffening elements define, at said second extremity, a full portion able, in an active configuration taken on by the elastically deformable stiffening elements themselves, to cover at least partially said first obstruction.

10. The device according to claim 1, further comprising a second obstruction of at least a second area of the intestine arranged along said tubular element and separated from said first obstruction, said second obstruction being movable between a relative tight configuration and a relative widened configuration respectively, to allow insertion inside the intestine itself and to prevent transit of intestinal contents through said second area of the intestine.

11. The device according to claim 10, wherein said first obstruction and said second obstruction are of an inflatable balloon type.

12. The device according to claim 11, further comprising a gap for inflation and a valve for deflation of said first obstruction and said second obstruction.

13. The device according to claim 1, wherein said entry openings are defined at a lateral surface of said first section.

14. The device according to claim 1, wherein at least some of said entry openings are arranged along a direction of longitudinal extension of said first section.

15. The device according to claim 1, wherein said entry openings have a substantially elliptical conformation.

16. A medical device for performing at least one of an ileostomy and a jejunostomy, comprising:

a tubular element comprising: a transit channel therethrough; a plurality of entry openings; and an exit opening; said tubular element being insertable within an intestine, wherein said tubular element further comprises a first section having said entry openings and configured for receiving faeces from said intestine; a second section having said exit opening configured for being positioned outside said intestine; and a middle portion between said first and second sections;

a first obstruction having opposite proximal and distal portions and extending around said middle portion of said tubular element between said first and second sections, said first obstruction configured to be: insertable with said tubular element inside said intestine in a tight configuration, and expandable to a widened configuration to prevent transit of said faeces through said intestine where said first obstruction has been inserted; and a stiffening member configured to help prevent at least said first section from bending, said stiffening member comprising:

at least one of (i) a distal ring-shaped first extremity and (ii) a distal cap-shaped first extremity that is attached to a distal end of said first section of said tubular element;

a proximal ring-shaped second extremity defining a through opening through which said tubular element extends;

a plurality of elastically deformable stiffening elements with each elastically deformable stiffening element having: (a) a distal end that is coupled to said at least one of said distal ring-shaped first extremity and said distal cap-shaped first extremity at said distal end of said first section of said tubular element and (b) a proximal end that is coupled to said proximal ring-shaped second extremity, wherein said proximal and distal portions of said first obstruction are disposed between said proximal ring-shaped second extremity and said at least one of said distal ring-shaped first extremity and said distal cap-shaped first extremity.

* * * * *